(12) United States Patent
Liu et al.

(10) Patent No.: US 7,419,960 B2
(45) Date of Patent: Sep. 2, 2008

(54) **HEMITERPENE GLYCOSIDES WITH ANTI-PLATELET AGGREGATION ACTIVITIES FROM *ILEX PUBESCENS***

(75) Inventors: Liang Liu, Kowloon Tong (HK); Zhihong Jiang, Kowloon Tong (HK); Min Li, Kowloon Tong (HK); Jingrong Wang, Kowloon Tong (HK); Zhongqiu Liu, Kowloon Tong (HK)

(73) Assignee: Hong Kong Baptist University, Hong Kong (HK)

( * ) Notice: Subject to any disclaimer, the term of this patent is extended or adjusted under 35 U.S.C. 154(b) by 352 days.

(21) Appl. No.: 11/031,415

(22) Filed: Jan. 7, 2005

(65) Prior Publication Data
US 2006/0154877 A1 Jul. 13, 2006

(51) Int. Cl.
*A01N 43/04* (2006.01)
*A61K 31/70* (2006.01)
*C07H 15/00* (2006.01)

(52) U.S. Cl. ............... 514/25; 536/4.1; 536/18.2
(58) Field of Classification Search ............. 514/25; 536/4.1, 18.2
See application file for complete search history.

(56) References Cited

U.S. PATENT DOCUMENTS
4,987,125 A 1/1991 Han et al.

OTHER PUBLICATIONS

Yang et al., "The vascular effects of *Ilex pubescens*", Planta Medica, 1986, 52:262-265.*
Han et al. "Anticoagulant Activity of Ilexoside D, a Triterpenoid Saponin from *Ilex pubescens*." Archives of Pharmacal Research, 1993, 16(3):209-212.
Qin et al. A Study on the Chemical Constituents of the Leaves of *Ilex pubescens* Hook et Arn var *glaber* Chang. III. Elucidation of the Structure of Gladeride I. A New Lignan Compound. *Acta Pharmaceutica Sinica*, 1980, 15(11):669-673.
Yang et al. "The Vascular Effects of *Ilex pubescens*." Planta Medica, 1986, 52:262-265.
Wang et al. "Effects of Ilex A Ingredient on Platelet Function and Shape." *Chinese Journal of Integrated Traditional and Western Medicine*, 1985, 5(4):232-234.
Jiang et al. "A Lupane Triterpene and Two Caffeates from *Rhoiptelea chiliantha*." *Phytochemistry*, 1995, 40(4):1223-1226.
Jiang, Z. H. "Two Diastereomeric Triterpene-Lignan Esters Having Dimeric Structure and Their Biosynthetically Related Triterpene Caffeate from *Rhoiptelea chiliantha*." *Tetrahedron Letters*, 1994, 35(13):2031-2034.
Jiang et al. "Caffeoyl, Coumaroyl, Galloyl, and Hexahydroxydiphenoyl Glucoses from *Balanophora japonica*." *Chem. Pharm. Bull.*, 2001, 49(7):887-892.
Jiang et al. "Dammarane-Type Triterpene Glycosides from the Leaves of *Rhoiptelea chiliantha*." *Chem. Pharm. Bull.*, 1999, 47(2):257-262.
Yu et al. "*neo*-Lignans and Hemiterpenoid from the Seeds of *Artabostrys hexapetalus* (Annonaceae)." *Journal of Chinese Pharmaceutical Sciences*, 2002, 11(1):4-10.
Toyota et al. "New Glycosides from the Japanese fern *Hymenophyllum barbatum*." *Chem. Pharm. Bull.*, 2002, 50(4):508-514.
Jiang et al. "Biflavanones, Diterpenes, and Coumarins from the Roots of *Stellera chamaejasme* L." *Chem. Pharm. Bull.*, 50(1):137-139.
Zeng et al. "Studies on the Chemical Structures of Ilexolide A." *Gaodeng Xuexiao Huaxue Xuebao*, 1984, *Chemical Journal of Chinese Universities*, 5(4):503-507.
Qin et al. "Studies on the Chemical Constituents of *Ilex pubescens* Hook et Am. II. The Structure of Ilexsaponin A." *Acta Chimica Sinica*, 1987, 45:249-255.
Hidaka et al. "New Triterpene Saponins from *Ilex pubescens*." *Chem. Pharm. Bull.*, 1987, 35(2):524-529.
Hidaka et al. "A Triterpene and Saponin from Roots of *Ilex pubescens*." *Phytochemistry*, 1987, 26(7):2023-2027.
Jiang et al. "Studies on the Chemical Constituents of *Ilex pubescens*. III. Isolations and Identifications of Four Saponin Glycosides." *Zhongcaoyao*, 1991, 22(7):291-294.

* cited by examiner

*Primary Examiner*—Shaojia Anna Jiang
*Assistant Examiner*—Traviss C McIntosh, III
(74) *Attorney, Agent, or Firm*—Knobbe, Martens, Olson & Bear LLP

(57) ABSTRACT

Two hitherto unreported novel hemiterpene glycosides were isolated in substantially pure form from the root of *Ilex pubescens*. The chemical structures and some properties of these hemiterpenes have been elucidated. These hemiterpene glycosides possess anti-platelet aggregation activity more potent than those of salvianolic acid B and aspirin and may be used in pharmaceutical compositions in humans and mammals in need of such treatment.

6 Claims, 1 Drawing Sheet

HEMITERPENE GLYCOSIDES WITH ANTI-PLATELET AGGREGATION ACTIVITIES FROM *ILEX PUBESCENS*

FIELD OF INVENTION

The present invention is related to novel botanical compounds with a pharmaceutical activity. In particular, the present invention relates to novel hemiterpene compounds.

BACKGROUND OF INVENTION

References which are cited in the present disclosure are not necessarily prior art and therefore their citation does not constitute an admission that such references are prior art in any jurisdiction. All references cited are hereby incorporated by reference in their entirety.

The dried root of the plant *Ilex pubescens* Hook. Et Arn. is known as "Mao-Dong-Qing" and is commonly used in Traditional Chinese Medicine (TCM) for the treatment of cardiovascular diseases and hypercholestaemia. Previous chemical investigations have reported isolation of triterpene saponins[1-6] and simple phenolics, i.e. 3,4-dihydroxyacetophenone, hydroquinone, scopoletin, esculetin, homovanillic acid, vomifoliol and glaberide from the roots and leaves of this plant[7].

Pharmacological researchers have demonstrated that extracts of "Mao-Dong-Qing" could not only enlarge blood vessels, but also improve mini-circulation, lower blood pressure, inhibit platelet aggregation, prevent thrombus, reduce cardiac ischemia, decline the excitation of the cardiac conduction system and enhance the ability of anoxia resistance of body[8]. However, the exact compounds contributing to these effects have not been fully identified.

In regard to the inhibitory effect of "Mao-Dong-Qing" on anti-platelet activation and aggregation, it was reported that ilexonin A, a semisynthesized succinate of pentacyclic triterpene which is the aglycone of the saponins in "Mao-Dong-Qing", could significantly inhibit platelet aggregation induced either by ADP (adenosine diphosphate) or AA (arachidonic acid) both in vivo and in vitro, and block 5-HT (5-hydroxytryptamine, serotonin) release by the platelets[9]. Other triterpenoids with antithrombotic activity isolated from *Ilex pubescens* have also been reported (Han et al, U.S. Pat. No. 4,987,125)[17].

Despite these findings, the anti-platelet activity of *Ilex pubescens* extract has not been elucidated and may also be due to other hitherto unidentified compounds as well. It is therefore an object of the present invention to further isolate and identify biologically-active compounds from *Ilex pubescens*.

SUMMARY OF INVENTION

The present invention relates to two substantially pure compounds pubescenoside A and pubescenoside B as well as their aglycone having the respective chemical formulae:

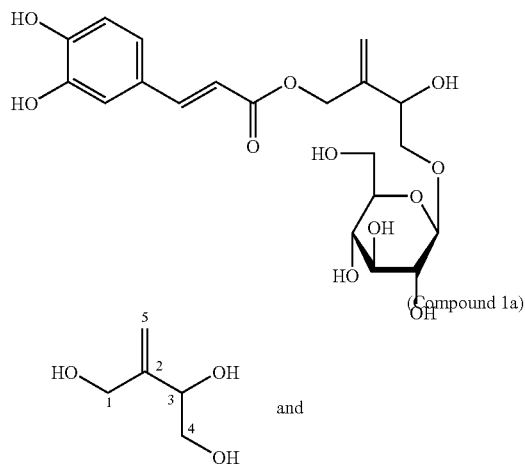
(Compund 1)

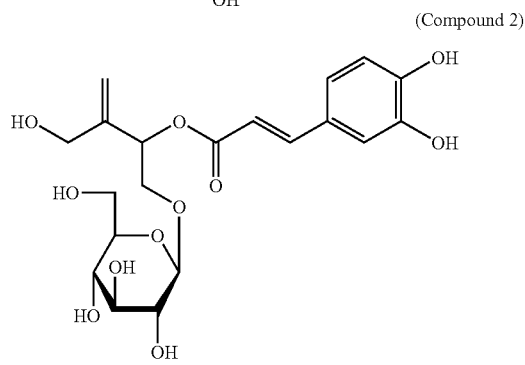
(Compound 1a)
and
(Compound 2)

The present invention also relates to a compound of Formula I or Formula II or a pharmaceutically acceptable salt, ester, amide, or prodrug thereof.

In one embodiment of the present invention, a substantially pure compound having the chemical formula shown below, or its pharmaceutically acceptable salt, ester, amide, or prodrug, is provided

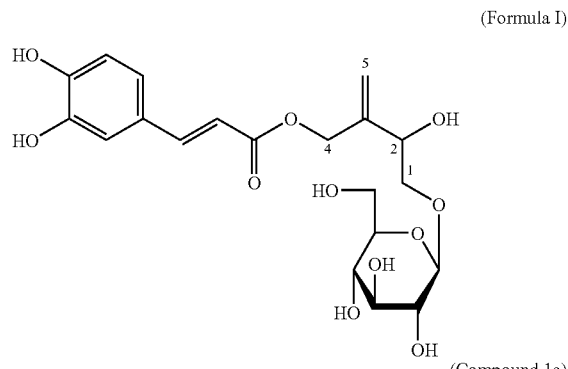
(Formula I)

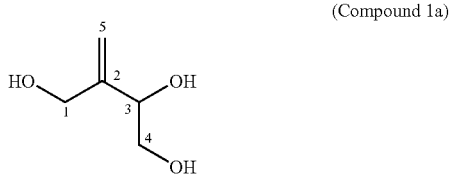
(Compound 1a)

In another embodiment of the present invention, a substantially pure compound having the chemical formula shown below, or its pharmaceutically acceptable salt, ester, amide, or prodrug, is provided (Formula II)

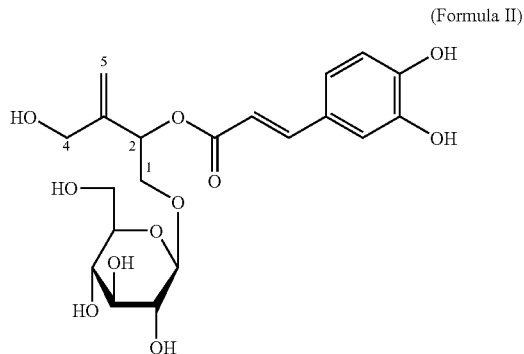

In yet a further embodiment of the present invention, a substantially pure compound which is a hemiterpene glycoside with 2-methylene-butane-1,3,4-triol as the aglycone is provided, wherein the hemiterpene is acylated by caffeic acid. The hemiterpene glycoside can be, for example pubescenoside A or pubescenoside B. The written description herein uses two different carbon numbering systems for the chemical structures of the glycosides (pubescenoside A or pubescenoside B) and aglycone (Compound 1a).

In an additional embodiment of the present invention, a pharmaceutical composition having a hemiterpene glycoside with 2-methylene-butane-1,3,4-triol as an aglycone is provided, wherein the hemiterpene is acylated by caffeic acid. The hemiterpene glycoside can be, for example pubescenoside A or pubescenoside B.

In a further embodiment of the present invention, a pharmaceutical composition to inhibit platelet aggregation in a mammal, having a pharmaceutically effective dose of a hemiterpene glycoside with 2-methylene-butane-1,3,4-triol as an aglycone, is provided, wherein the hemiterpene is acylated by caffeic acid. The hemiterpene glycoside can be, for example pubescenoside A or pubescenoside B.

In yet another embodiment of the present invention, a method of isolating at least one hemiterpene glycoside from a plant material is provided, by mechanically reducing the plant material, extracting the reduced materials with a first solvent to form an extract, and purifying the hemiterpene glycoside from the extract to a desired purity. The plant material can be, for example, the dried root of *Ilex pubescens*. The plant material can be mechanically reduced, for example, by chopping and grinding the plant material to powder. The first solvent can be methanol, and the extracting step can also involve the addition of water to the extract. The purifying step can involve, for example, partitioning the extract with diethyl ether, ethyl acetate and n-butanol to obtain four fractions, subjecting the n-butanol fraction to gel chromatography eluted with gradient methanol ranging from 0% to 100% to obtain a plurality of fractions, subjecting the fractions eluted by 45% to 65% methanol to thin layer chromatography, visualizing components separated by the thin layer chromatography with ferrous chloride, and subjecting components visualized by the ferrous chloride to a further purification step. The purification step can also involve at least one of the following techniques: gel chromatography, thin layer chromatography, and column chromatography.

In another embodiment of the present invention, a method of treating a disorder related to blood platelets in a mammal is provided, by administering a pharmaceutically effective dose of a hemiterpene glycoside, wherein the hemiterpene glycoside has 2-methylene-butane-1,3,4-triol as an aglycone and where the hemiterpene is acylated by caffeic acid. The hemiterpene glycoside can be, for example pubescenoside A or pubescenoside B.

The present invention also relates to substantially pure hemiterpene glycosides with 2-methylene-butane-1,3,4-triol as the aglycone and where the hemiterpene is acylated by caffeic acid. The invention also relates to pharmaceutical compositions comprising such hemiterpene glycosides. Such pharmaceutical compositions comprising the hemiterpene glycosides of the present invention may be used to treat disorders related to blood platelets in a mammal such as human being.

The present invention further relates to a method of isolating hemiterpene glycosides from plant materials containing these compounds, the method comprising the steps of mechanically reducing the plant material, extracting the reduced material with a first solvent and then purifying hemiterpene glycosides from the extraction to a desired purity.

The most preferred embodiment of this aspect of the present invention comprises providing the dried root of *Ilex pubescens*; mechanically reducing the root to a powder; extracting the powder with alcohol to form an extract; suspending the extract in water; subjecting the suspension thus formed to liquid-liquid partitioning by successively adding diethyl ether, ethyl acetate, and n-butanol to form fractions; subjecting the n-butanol fraction to gel chromatography eluted by gradient methanol; subjecting the fractions eluted by 30% to 70% methanol to thin layer chromatography to separate any components therein; applying ferrous chloride to the thin layer chromatography plate to visualize the components; successively subjecting the components thus visualized to gel chromatography, thin layer chromatography and column chromatography to yield the hemiterpene glycosides.

DETAILED DESCRIPTION

Figure 1:
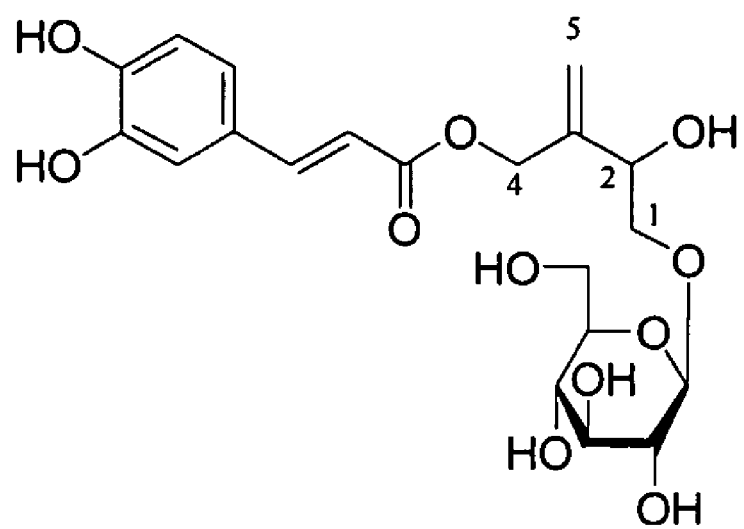
FIG. 1 shows the chemical structure of Compound 1 (pubescenoside A).

The present invention relates to two substantially pure compounds pubescenoside A and pubescenoside B having the respective chemical formulae:

(Compund 1)

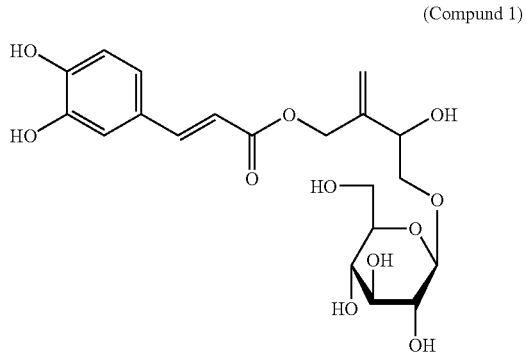

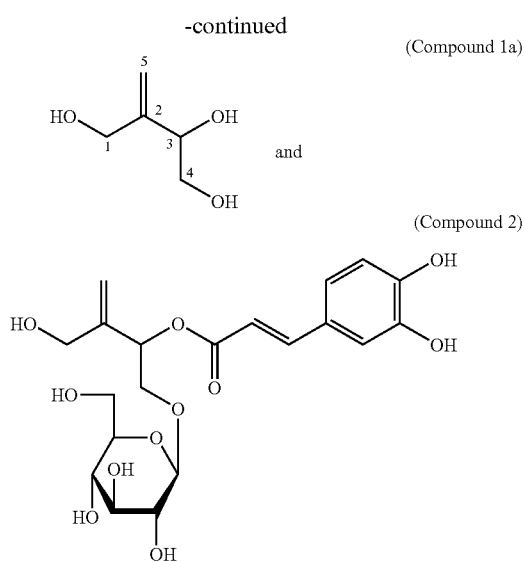

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The term "ester" refers to a chemical moiety with formula —$(R)_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —$(R)_n$—C(O)NHR' or —$(R)_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, $3^{rd}$ Ed., John Wiley & Sons, New York, N.Y., 1999, which is incorporated herein in its entirety.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

As used in the present specification and claims, the terms "comprise," "comprises," and "comprising" mean "including, but not necessarily limited to". For example, a method, apparatus, molecule or other item which contains A, B, and C may be accurately said to comprise A and B. Likewise, a method, apparatus, molecule or other item which "comprises A and B" may include any number of additional steps, components, atoms or other items as well.

Also, unless otherwise defined, all technical and scientific terms used herein have the same meaning as commonly understood by one of ordinary skill in the art to which this invention belongs. Although any methods or materials similar to those described herein can be used in the practice or testing of the present invention, only the preferred embodiments are described. Utilizing the description below, a person skilled in the art of the preparation and use of Chinese herbal medicine can readily practice the methods of the present invention.

While dried material is traditionally used and preferred in Chinese herbal medicine, it must be recognized that drying of plant materials facilitates their storage, transportation and subsequent processing. Drying may not be a requirement to derive the benefits of these herbs. As such, it is understood that the present invention may be practiced with the corresponding quantity of the listed fresh plant materials as well. The use of fresh plant materials, sufficient to meet the requisite quantity and proportions of the extracts used, come under the scope of the present invention.

Also, while the root of *Ilex pubescens* is preferred as the plant part for use as it has the highest concentration of the compounds of interest, other parts of this plant may also be similarly used.

In this description, the term "substantially pure" as it refers to the isolation of the compounds of the present invention means a chemical purity of at least 75%, preferably 85-100%, more preferably 90-100% and most preferably 95-100%.

In a first aspect, the present invention relates to two first novel hemiterpene compounds among other compounds isolated from the plant *Ilex pubescens* with anti-platelet aggregation activity in humans and mammals. These two first novel compounds have hitherto not been reported as borne out by searches on authoritative databases such as Chemical Abstracts, Medline and Science Citation Index.

These two first novel compounds are also distinguished from the previously reported compounds associated with *Ilex pubescens*. For example, Ilexonin A is a semi-synthesized compound which is a succinic acid ester of triterpene (the triterpene was obtained from acid hydrolysate of the saponins of "Mao-Dong-Qing"). It is not an original component in "Mao-Dong-Qing" and it belongs to completely different type of compound compared to pubescenosides A and B.

In another aspect, the present invention relates to pharmaceutical formulations comprising at least one of the novel compounds of the present invention possessing anti-platelet aggregation activity for the treatment of a human or mammal in need of such treatment.

In yet another aspect, the present invention relates to the isolation (extraction, purification and structural elucidation) of these two compounds. The isolation is described followed by the determination of their anti-platelet aggregation activity against other known compounds with this pharmaceutical activity. The formulation of a pharmaceutical composition comprising at least one of these compounds is also taught.

Materials and Methods

Overview of the Approach. "Mao-Dong-Qing", the root of *Ilex pubescens* Hook et Arn. was mechanically reduced and extracted with methanol three times to yield a total extract. The total extract was then subjected to liquid-liquid partition to yield several fractions. Tests on these fractions indicated that some phenolic compounds positive to $FeCl_3$/EtOH reagent in thin-layer chromatography exist in one of the fractions, an alcoholic (n-BuOH) fraction. Subsequent experimental procedures were directed to the isolation of compounds in this layer for pharmacological screening. The n-BuOH layer of the methanol extracts was subjected to gel chromatography over a combination of MCI-gel CHP 20P, TSK Toyopearl HW-40 and ODS to yield two novel compounds of the present invention which are hereby named pubescenosides A and B (Compunds 1 and 2 respectively). These two compounds are the first two identified by us in *Ilex pubescens* by this extraction method.

Plant Material. Dried root of *Ilex pubescens* was purchased from the Pharmacy of Chinese Medicine Clinic of Hong Kong Baptist University (HKBU) and was identified by Dr. Zhongzhen Zhao of the School of Chinese Medicine at HKBU. For future verification in the future should such be warranted, the voucher specimen was deposited in the Centre of Chinese Materia Medica Speciemen, HKBU.

General Equipment. Optical rotations were measured with a Jasco P-1010 polarometer. $^1H$ and $^{13}C$ nuclear magnetic resonance (NMR) data were recorded on a Bruker AV-500 (500 MHz for $^1H$ and 125 MHz for $^{13}C$) and Varian Mercury-Plus 300 MHz nuclear magnetic resonance (NMR) spectrometer. Coupling constants were given in Hz and chemical shifts were represented in δ (ppm). High resolution mass spectrometry (HR-MS) was preformed on a QSTAR Pulsar i time-of-flight (TOF) mass spectrometer. High performance liquid chromatograph (HPLC) was carried on an Agilent Series 1100 HPLC equipped with Agilent G1315A diode array detector (DAD) Detector and Alltech Evaporative Light Scattering Detector. Column chromatography was performed with MCL-gel CHP 20P (75-150 μm, Mitsubishi Chemical Corporation), Chromatorex octadecylsilica (ODS) (100-200 mesh, Fuji Silysia Chemical Ltd.), Toyopearl HW-40F (Tosoh Corporation). Thin layer chromatography (TLC) was carried out on precoated Kieselgel 60 F254 plate (0.2 mm thick, Merck KGaA) and the spots were detected by ultraviolet (UV) illumination and by spraying with 2% ethanolic $FeCl_3$ and 10% sulfuric acid reagent.

Extraction and Isolation. The dried plant material (1.2 kg) was mechanically reduced, preferably to powder by chopping and grinding, and extracted with methanol (28 L) at room temperature three times to yield 68 g of a total extract. The total extract was suspended in water and then subjected to liquid-liquid partition. This is preferably done by successive addition of three solvents, diethyl ether, ethyl acetate and n-butanol, to yield four fractions, i.e. $Et_2O$ layer (2.9 g), EtOAc layer (15.1 g), n-BuOH layer (30.7 g) and $H_2O$ layer (20.0 g).

The n-BuOH layer was chromatographed over MCL-gel CHP 20P eluted with gradient methanol in water to afford 6 fractions. All these fractions were monitored and detected by silica gel thin-layer chromatography [$CHCl_3$-MeOH-$H_2O$ (8:2:0.2); (7:3:0.5)]. Two of the fractions eluted by 50% and 60% MeOH which were positive to $FeCl_3$ reagent and were further subjected to column chromatography on Chromatorex ODS gel (20-60% MeOH) and Toyopearl HW-40F gel (30-60% MeOH) to yield compounds 1 (162 mg) and 2 (256 mg).

These two compounds are named Pubescenoside A (compound 1) and Pubescenoside B (compound 2) respectively.

Identification of Isolated Compounds

Pubescenoside A (Compound 1): A pale-yellow amorphous powder. $[\alpha]_D^{21}=-17.4°$ (c=0.1, MeOH). High-Resolution ESI-Q-TOF (Positive ion mode) m/z 465.1339 [M+Na]$^+$ (Calculated for $C_{20}H_{26}O_{11}Na$: 465.1365). The $^1H$- and $^{13}C$-NMR data were presented in Table 1.

Acid hydrolysis of pubescenoside A: A solution of compound 1 (10 mg) in 2N HCl (4 ml) was heated at 90° C. for 3 hr. The reaction mixture was neutralized with 5% NaOH and then extracted with EtOAc. Chromatography and co-chromatography of the EtOAc extract was performed with caffeic acid by silica gel TLC [CHCl3-EtOAc-Toluene-HCOOH-MeOH (15:20:10:10:1), $R_f$=0.45] and HPLC [Ailtech Altima $C_{18}$ (4.6×250 mm); 0-30% (40 min) $CH_3CN$ in $CH_3CN:H_2O$: HCOOH (10:90:0.4); Flow rate: 1.0 ml/min; Detection wavelength: UV 280 nm, $t_R$=15.60 minute] confirmed the existence of caffeic acid. The water layer was evaporated to dryness and chromatographed on silica gel using $CHCl_3$-MeOH-$H_2O$ (9:1:0.1, 8:2:0.2, 7:3:0.5) as mobile phase to give compound 1a (1 mg) and D-(+)-glucose, which was identified by HPLC [Alltech Prevail Amino Column (2.1× 150 mm), solvent system: $CH_3CN$-$H_2O$ (90:10 v/v) at flow rate of 0.3 ml/min, detection: ELSD detector (Tube temperature: 95° C., $N_2$ gas at flow rate of 1.0 ml/min), $t_R$=11.83 minute ($t_R$ of standard sugars mannose, glucose and galactose are 10.49, 11.78 and 12.48 min, respectively] and co-chromatography with authentic D-(+)-glucose as reference. Configuration of the glucose was determined to be D-form by its rotation value $[\alpha]_D^{22}=+43.7°$ [(c=0.04, $H_2O$), determined after being dissolved in $H_2O$ for 24 hours, and the concentration of glucose was determined by HPLC].

Compound 1a is 2-methylene-butane-1,3,4-tri-ol: colorless oil; $[\alpha]_D^{21}=+21.2°$ (c=0.04, MeOH); $^1H$-NMR (300 MHz, $C_5D_5N$) δ: 5.63 (2H, s, H-5), 4.91 (1H, dd, J=5.2, 7.2 Hz, H-2), 4.71 (2H, s, H-4), 4.24 (1H, dd, J=10.8, 5.2 Hz, H-1), 4.16(dd, J=10.8, 7.2 Hz, H-1).

Pubescenoside B (Compound 2): A pale-yellow amorphous powder. $[\alpha]_D^{21}=-28.7°$ (c=0.1, MeOH). High-Resolution ESI-Q-TOF (Positive ion mode) m/z 465.1377 (M+Na)$^+$ (Calculated for $C_{20}H_{26}O_{11}Na$: 465.1365). The $^1H$- and $^{13}C$-NMR data were presented in Table 1.

Acid hydrolysis of pubescenoside B: Compound 2 (15 mg) was hydrolyzed in a manner similar to that described for compound 1, yielding caffeic acid, D-(+)-glucose $\{[\alpha]_D^{21}=+33.1°$ (c=0.1, $H_2O$), determined after being dissolved in $H_2O$ for 24 hours} and compound 1a which was identified by comparing its $^1H$-NMR data with those described in the reference[13].

While the preparation of the specific embodiments of the present invention are taught above, those skilled in the art would be able to prepare the full range of the claimed compounds using methods analogous to those illustrated above, as well as to scale up isolation and purification of the compounds for industrial pharmaceutical use.

Assay of Biological Activity

Preparation of platelet-rich-plasma (PRP): Sprague-Dawley rats (350-450 g) were used as blood donors to collect anticoagulated blood. Collected blood samples were immediately transferred into a plastic tube anticoagulant (1/10 volume of 3.8% trisodium citrate, pH 7.4). The platelet-rich-plasma (PRP) was then prepared by centrifuging the blood at 300 rpm for 15 minutes. The platelet concentration was adjusted to a level of $5 \times 10^5/\mu l$ by addition of homologous platelet-poor-plasma (PPP) obtained after further centrifugation of blood at 1500 rpm for 15 minutes. For getting sufficient amount of PRP, at least two rats have to be sacrificed each time to obtain a pooled PRP sample.

Shear-induced platelet aggregation (SIPA): Adjusted PRP was divided into different groups according to the experimental protocol, mixed with 10 μM of pubescenosides A, B, aspirin and Salvianolic acid B. HAAke Rheometer RS 600 (Thermo Haake Corp., Ltd., Germany) with sensor C60/0.5° was employed as shear generator. The rheometer has the benefit of controlling shear stress and with an accuracy of 1 μm by the automatic adjustment of the gap between cone and plate. The shear program for PRP is: preheating sample at 37° C., increasing stress level from 0 to 15 Pa in the duration of 30 seconds, and then maintaining the stress level at 15 Pa for 360 seconds. After shearing, PRP was transferred to a platelet aggregometer (Chrono-Log aggregometer, Model 560 CA, Chrono-Log Corp., U.S.A) and SIPA was determined by turbidity. Since platelet-poor-plasma (PPP) and the pre-shear PRP were used as the turbidity scales of 100% and 0% aggregation, respectively, the aggregative degree of post-shear PRP could be measured.

Results and Discussion

Pubescenoside A (Compound 1)

Pubescenoside A (Formula I) (Compound 1) was isolated as a pale-yellow powder and showed positive reaction to $FeCl_3$/EtOH reagent in thin-layer chromatography. The positive ESI-Q-TOF mass spectrum of Compound 1 gave an $[M+Na]^+$ ion peak at m/z 465.1377 indicating its molecular formula is $C_{20}H_{26}O_{11}$. Its $^1H$-NMR and $^{13}C$-NMR data (Table 1) suggested the presence of the moieties of a caffeoyl[10-12] and a β-glucose [anomeric proton at $\delta_H$ 4.33 (J=7.8 Hz) and anomeric carbon at $\delta_C$ 104.5][13] in the molecule. The remaining five non-aromatic carbons signals in the $^{13}C$-NMR spectrum implied the presence of a hemiterpene moiety in the molecule of compound 1. By detailed analysis of the $^1H$-NMR spectral data, the signals attributed to an exomethylene proton at δ 5.25 (1H, brs) and δ 5.34 (1H, brs), and 1,2-glycol unit as evidenced by a $^1H$-$^1H$ coupling between the oxygenated methine signal at δ 4.42 (1H, dd, J=6.8, 3.6 Hz, H-2) and one of the oxygenated methylene signal at δ 3.91 (1H, dd, J=10.8, 6.8 Hz, H-1) were observed. The heteronuclear multiple bond correlation (HMBC) spectra showed correlation between the exomethylene proton signal and the carbon [δ72.3 (C-3)] bearing to the secondary hydroxyl group of the 1,2-glycol unit. The $^1H$-$^{13}C$ long-range correlation between the exomethylene proton signal and the oxygenated carbon signal at δ 65.4 (C-4) were also confirmed in HMBC spectrum of Compound 1. These led to the elucidation of a 2-methlene-1,3,4-trioxygenated butane structure as the aglycone of Compound 1. The carbon numbering of aglycone (Compound 1a) herein uses a different numbering system from that of glycosides (Compound 1 and 2), as mentioned above. The location of caffeoyl group was determined to be at C-4 position of Compound 1 since correlation between the carbonyl carbon (δ168.8) of caffeoyl group and H-4 proton signals at δ 4.79 and 4.73 was observed in the HMBC spectra (FIG. 1). The anomeric proton signal of the β-glucosyl group at $\delta_H$ 4.31 (J=7.8 Hz) showed obvious correlation with C-1 signal at $\delta_C$ 74.0, indicating the glucosylation position to be at C-1 of Compound 1. The acid hydrolysis of Compound 1 afforded caffeic acid, D-glucose ($[\alpha]_D^{22}=+43.7°$) which were confirmed by HPLC comparison with the authentic samples and aglycone 1a ($[\alpha]_D^{21}=+21.2°$) which was identified as an enantiomer of the hemiterpene isolated from *Artabostrys hexapetalus*[14] and the aglycone of the glycoside isolated from Japanese fern *Hymenophyllum barbatum*[15]. On the basis of the above results, the structure of Compound 1 (pubescenoside A) was established as 4-caffeoyloxy-2-hydroxy-3-methylene-butane-1-O-β-D-glucopyranoside.

TABLE 1

$^1H$ (500 MHz) and $^{13}C$ (125 MHz) NMR Spectral Data (δ) of Compounds 1 and 2 (in CD3OD)

| position | 1 C | 1 H | 2 C | 2 H |
|---|---|---|---|---|
| 1 | 74.0 t | 3.91 dd (10.8, 6.8) | 71.9 t | 4.12 dd (11.2, 7.6) |
|   |        | 3.76 dd (10.8, 3.6) |         | 3.85 dd (11.2, 3.6) |
| 2 | 72.3 d | 4.42 dd (6.8, 3.6)  | 74.6 d  | 5.58 dd (7.6, 3.6)  |
| 3 | 145.4 s |                    | 147.1 s |                     |
| 4 | 65.4 t | 4.79 d (13.5)       | 63.9 t  | 4.18 d (13.5)       |
|   |        | 4.73 d (13.5)       |         | 4.14 d (13.5)       |
| 5 | 114.6 t | 5.25 br s          | 113.3 t | 5.25 d (1.0)        |
|   |        | 5.34 br s           |         | 5.23 d (1.0)        |
| caf-1 | 127.4 s |                |  127.7 s |                    |
| caf-2 | 115.1 d | 7.04 d (2.0)   | 115.2 d | 7.04 d (2.0)        |
| caf-3 | 147.0 s |                | 146.8 s |                     |
| caf-4 | 150.1 s |                | 149.7 s |                     |
| caf-5 | 116.6 d | 6.76 d (8.0)   | 117.1 d | 6.77 d (8.0)        |
| caf-6 | 123.1 d | 6.94 dd (8.0, 2.0) | 123.0 d | 6.95 dd (8.0, 2.0) |
| caf-7 | 147.3 d | 7.56 d (15.6)  | 147.3 d | 7.57 d (16.0)       |
| caf-8 | 114.8 d | 6.27 d (15.6)  | 115.1 d | 6.28(d (16.0)       |
| caf-9 | 168.8 s |                | 168.5 s |                     |
| Glc-1 | 104.3 d | 4.31 d (7.8)   | 104.5 d | 4.33 d (7.8)        |
| Glc-2 | 75.0 d | 3.22 dd (7.8, 9.0) | 75.0 d | 3.18 dd (7.8, 9.0) |
| Glc-3 | 77.9 d | 3.36 m          | 78.1 d | 3.33 m              |
| Glc-4 | 71.5 d | 3.30 m          | 71.5 d | 3.30 m              |
| Glc-5 | 78.0 d | 3.29 m          | 78.1 d | 3.28 m              |
| Glc-6 | 62.7 t | 3.65 m          | 62.7 d | 3.65 dd (12.0, 2.4) |
|       |        | 3.85 dd (12.0, 1.6) |    | 3.82 m              |

Assignments were established on the basis of $^1H$-$^1H$ COSY, HSQC and HMBC spectral data.

Pubescenoside B (Compound 2)

Figure 2:
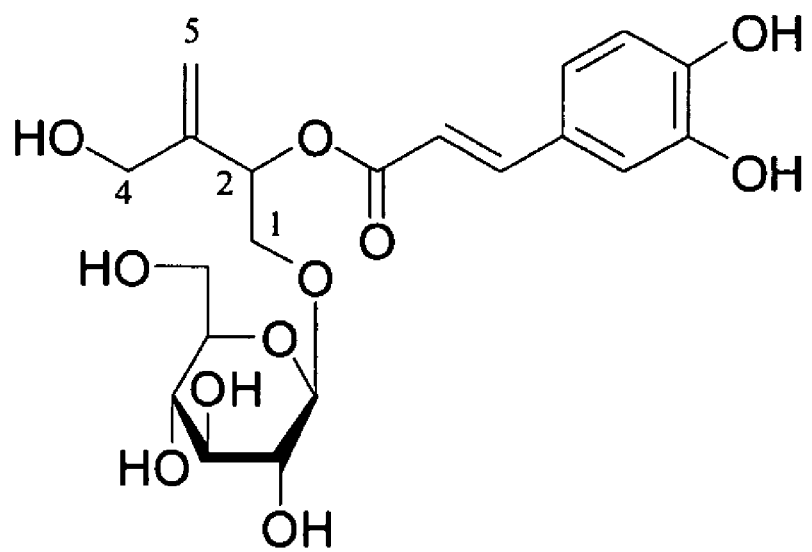
FIG. 2 shows the chemical structure of Compound 2 (pubescenoside B).

Pubescenoside B (Formula II) (Compound 2) was also isolated as a pale-yellow powder showing positive reaction with $FeCl_3$ in TLC. Its ESI-Q-TOF mass spectrometry showed a quasimolecular ion peak at m/z 465.1339 (corresponding to $C_{20}H_{26}O_{11}Na$) demonstrating that it is an isomer of Compound 1. Careful examination of the $^1H$-NMR and $^{13}C$-NMR spectra of Compound 2 suggested the existence of a caffeoyl group, a glucose moiety and a hemiterpene moieties in its molecule, showing great similarity with Compound 1. These results indicated that Compound 2 is also a hemiterpene glycoside acylated by caffeic acid. By comparing its $^1H$-NMR data with those of Compound 1, it is found that a large down-field shifts of H-2 ($\Delta\delta_H=+1.16$ ppm) was observed, suggesting that caffeoyl group is located at C-2 position of Compound 2. The HMBC experiments provided further evidence for this conclusion because a correlation between the carbonyl carbon (δ 168.5) of caffeoyl group and H-2 proton signal at δ5.58 (dd, J=7.6, 3.6 Hz) was observed (FIG. 2). Furthermore, the anomeric proton signal of the β-glucosyl group at $δ_H$ 4.33 (J=7.8 Hz) showed strong correlation with C-1 at $δ_C$ 71.9 in the HMBC spectrum which determined the glucose linkage at C-1 position of Compound 2. Acid hydrolysis of Compound 2 in a condition similar with that for the acid hydrolysis of Compound 1 afforded caffeic acid, D-glucose ($[α]_D^{22}$=+33.1°) and aglycone 1a which was confirmed by $^1$H-NMR spectral data. On the above spectral and chemical evidence, Compound 2 (pubescenoside B) was concluded to be 4-hydroxy-2-caffeoyloxy-3-methylene-butane-1-O-β-D-glucopyranoside.

Thus, the Compound 1 (pubescenoside A) and Compound 2 (pubescenoside B) may be described as hemiterpene glycosides with 2-methylene-butane-1,3,4-triol as the aglycone and where the hemiterpenes are acylated by caffeic acid.

Both pubescenosides A and B belong to the family of hemiterpene glycosides whose existence is very rare in the nature. No more than 40 such hemiterpenes have been isolated from plants so far. Among several types of hemiterpenes, 2-methylene-butane-1,3,4-triol, the aglycone of pubescenosides A (Compound 1) and B (Compound 2), is especially unusual. Only three hemiterpenes possessing this structure were reported till now, one was isolated from an Annonaceae plant[14], the other two were obtained from Japanese ferns[15]. Pubescenosides A and B are the first hemiterpene glycosides to be reported with 2-methylene-butane-1,3,4-triol as the aglycone which are further acylated by caffeic acid.

The pharmacological effects of pubescenosides A and B on anti-platelet aggregation were assayed with a series of repeatable experiments of high shear stress-induced platelet activation and aggregation test as described in the section on assay of biological activity above. The results (Table 2) indicated that anti-platelet aggregation activities of pubescenosides A and B are even much stronger than that of salvianolic acid B, an active ingredients from Chinese herb Radix Salviae Miltiorrhizae ("Danshen") and aspirin, a well-known Western drug for anti-platelet aggregation.

TABLE 2

Activities of pubescenosides A, B, salvianolic acid B and aspirin on anti-platelet aggregation

| Sample | Concentration (μM) | n | Platelet aggregation rate (%) ($\bar{X}$ ± SD) |
|---|---|---|---|
| Control | 10 | 10 | 54.400 ± 8.592 |
| Pubescenoside A | 10 | 10 | 36.550 ± 7.697*■▲ |
| Pubescenoside B | 10 | 10 | 27.300 ± 10.263*□ |
| Aspirin | 10 | 10 | 44.700 ± 4.668* |
| Salvianolic acid B | 10 | 10 | 39.650 ± 8.577* |

*vs. Control P < 0.05;
□vs. Aspirin P < 0.05;
■vs. Aspirin P < 0.01
▲vs. Salvianolic acid B P < 0.01

A person skilled in the art will appreciate that other novel compounds, particularly other hemiterpenes may be isolated by the method taught.

A person skilled in the art also will appreciate that a pharmaceutical composition comprising at least one of the novel compounds of the present invention may be readily prepared for use as an active compound for an anti-platelet aggregation medication that may be administered orally or by injection.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like.

Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols.

When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoylresidues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

Conclusion

Two hitherto unreported novel hemiterpene glycosides were isolated in substantially pure form from the root of *Ilex pubescens*. The chemical structure and some properties of these hemiterpene glycosides have been elucidated and are named pubescenoside A and pubescenoside B by the inventors. These hemiterpene glycosides possess anti-platelet aggregation activity more potent than those of salvianolic acid B and aspirin and may be used either alone or in combination in pharmaceutical compositions in humans and mammals in need of such treatment.

REFERENCES

Articles of the scientific and patent literature cited herein are hereby incorporated in their entirety by reference by such citation.
(1) Zeng, L. M.; Su, J. Y.; Zhang, S. Gaodeng *Xuexiao Huaxue Xuebao*, 1984, 5, 503-508
(2) Qin, G. W.; Chen, Z. X; Xu, R. S.; Jiang, Z. F.; Liang, J. G. *Huaxue Xuebao*, 1987, 45:249-255
(3) Hidaka, K.; Ito, M.; Matsuda, Y.; Kohda, H.; Yamasaki, K.; Yamahara, J.; Chisaka, T.; Kawakami, Y.; Sato, T.; Kagei, K. *Chem. Pharm. Bull.* 1987, 35:524-529
(4) Hidaka, K.; Ito, M.; Matsuda, Y; Kohda, H.; Yamasaki, K.; Yamahara, J. *Phytochem.* 1987, 26:2023-2027
(5) Jiang, Z. F.; Huang, R. X.; Qin, G. W.; Tian, Y.; Xu, R. S. *Zhongcaoyao*, 1991, 22:291-294
(6) Han, Y N; Song, J. I.; Rhee, I. K. *Archives of Pharmacal Research*, 1993, 16:209-212
(7) Qin, W. J.; Jiao, Z. Y; Fan, Z. T.; Ghen, B. Q.; Lin, X. Y.; Yao, J. X. *Yaoxue Xuebao*, 1980, 15: 669-673
(8) Yang, M. L.; Pang, K. T. *Planta Medica*, 1986, 52:262-265
(9) Wang, Z.; Du, J. X.; Zhu, G. Q.; Chinese Journal of Integrated Traditional and Western Medicine, 1985, 5:232-234
(10) Jiang, Z. H.; Tanaka, T.; Kouno, I. *Phytochemistry*, 1995, 40:1223-1226
(11) Jiang, Z. H.; Tanaka, T.; Kouno, I. *Tetrahedron letters*, 1994, 35:2031-2034
(12) Jiang, Z. H.; Hirose, Y.; Iwata, H.; Sakamoto, S.; Tanaka, T.; Kouno, I. *Chem. Pharm. Bull.*, 2001, 49:887-892
(13) Jiang, Z. H.; Fukuoka, R.; Aoki, F.; Tanaka, T.; Kouno, I. *Chem. Pharm. Bull.*, 1999, 47:257-262
(14) Yu, J. G.; Li, T. M.; Sun, L.; Luo, X. Z.; Ding, W.; Li, D. Y. *Journal of Chinese Pharmaceutical Sciences*, 2002, 11:4-10
(15) Toyota, M.; Oiso, Y.; Asakawa, Y. *Chem. Pharm. Bull.*, 2002, 50:508-514
(16) Jiang, Z. H.; Tanaka, T.; Sakamoto, T.; Kouno, I. *Chem. Pharm. Bull.*, 2002, 50:137-139
(17) Han, Y. H.; Han B. H.; Baik S. K.; Kim T. H. U.S. Pat. No. 4,987,125.

What is claimed is:

1. A substantially pure isolated compound of at least 75% chemical purity comprising a hemiterpene glycoside that has an aglycone of a chemical formula of 2-methylene-butane-1,3,4-triol and is acylated by caffeic acid.

2. The compound of claim 1 having the structural formula:

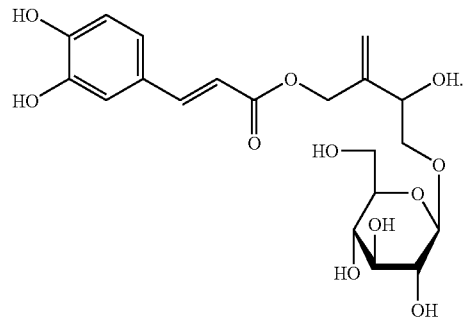

3. The compound of claim 1 having the structural formula:

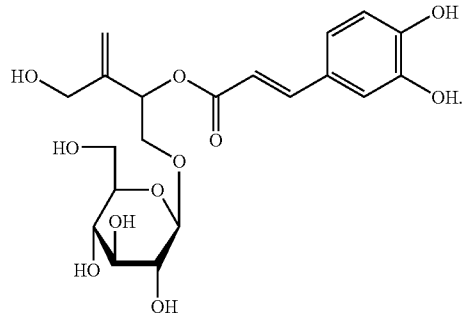

4. A pharmaceutical composition comprising the compound of claim 1 and a pharmaceutically acceptable carrier.

5. A pharmaceutical composition comprising the compound of claim 2 and a pharmaceutically acceptable carrier.

6. A pharmaceutical composition comprising the compound of claim 3 and a pharmaceutically acceptable carrier.

* * * * *